(12) United States Patent
Zivitz et al.

(10) Patent No.: US 7,998,069 B2
(45) Date of Patent: Aug. 16, 2011

(54) MASK ALGORITHMS FOR HEALTH MANAGEMENT SYSTEMS

(75) Inventors: Maury Zivitz, Indianapolis, IN (US); Paul Galley, Indianapolis, IN (US); Lois Jovanovic, Santa Barbara, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 281 days.

(21) Appl. No.: 11/853,467

(22) Filed: Sep. 11, 2007

(65) Prior Publication Data

US 2009/0069636 A1   Mar. 12, 2009

(51) Int. Cl.
*A61B 5/00* (2006.01)

(52) U.S. Cl. .......................... 600/300; 600/301; 706/924

(58) Field of Classification Search .......... 600/300–301, 600/365
See application file for complete search history.

(56) References Cited

U.S. PATENT DOCUMENTS

| | | | |
|---|---|---|---|
| 4,340,977 A | | 7/1982 | Brownlee et al. |
| 4,731,726 A | * | 3/1988 | Allen, III ...................... 600/300 |
| 5,251,126 A | * | 10/1993 | Kahn et al. .................... 600/309 |
| 5,762,625 A | | 6/1998 | Igaki |
| 6,299,637 B1 | | 10/2001 | Shaolian et al. |
| 6,379,301 B1 | * | 4/2002 | Worthington et al. ........ 600/309 |
| 6,923,763 B1 | * | 8/2005 | Kovatchev et al. ............ 600/300 |
| 7,651,845 B2 | * | 1/2010 | Doyle et al. ..................... 435/14 |
| 2004/0059201 A1 | | 3/2004 | Ginsberg |
| 2005/0192494 A1 | | 9/2005 | Ginsberg |
| 2005/0215868 A1 | | 9/2005 | Kenjou et al. |
| 2005/0272640 A1 | | 12/2005 | Doyle, III et al. |
| 2006/0272652 A1 | | 12/2006 | Stocker et al. |
| 2007/0016449 A1 | | 1/2007 | Cohen et al. |
| 2007/0033074 A1 | | 2/2007 | Nitzan et al. |
| 2008/0234943 A1 | * | 9/2008 | Ray et al. ......................... 702/19 |

FOREIGN PATENT DOCUMENTS

| | | |
|---|---|---|
| EP | 1 281 351 | 2/2003 |
| WO | WO2005/093629 | 10/2005 |
| WO | WO 2007/005170 | 1/2007 |
| WO | WO2007/112034 | 10/2007 |

OTHER PUBLICATIONS

International Search Report for International Application No. PCT/EP2008/007459, 10 pages.
International Preliminary Report on Patentability, PCT/EP2008/007459, Sep. 17, 2009.

* cited by examiner

*Primary Examiner* — Eric F Winakur
*Assistant Examiner* — Shirley Jian
(74) *Attorney, Agent, or Firm* — Baker & Daniels LLP

(57) ABSTRACT

A device and method of providing information to a healthcare provider regarding the dosing of insulin is provided where the data is analyzed to produce a qualified set of points. The applied analysis is performed via parameters that are independent of patient input.

19 Claims, 6 Drawing Sheets

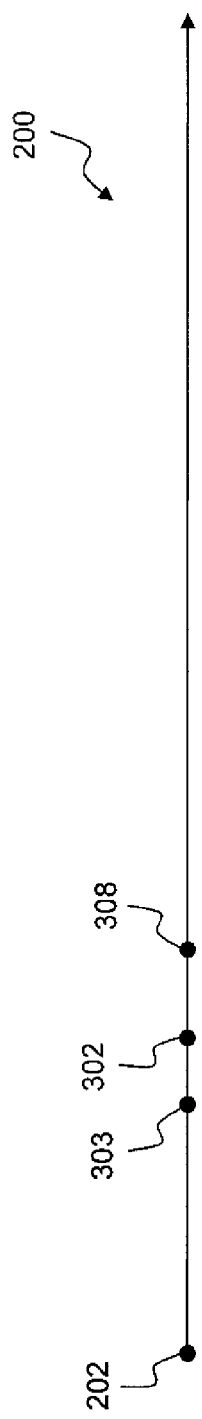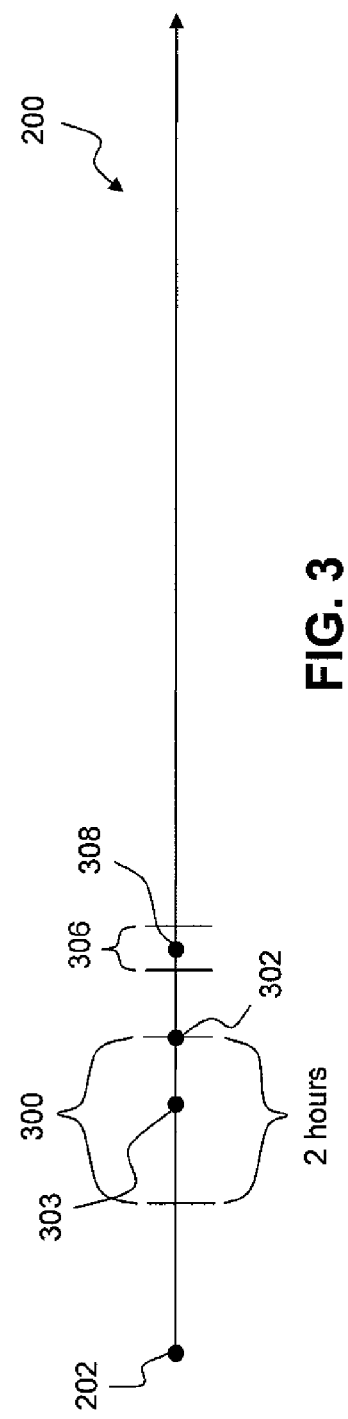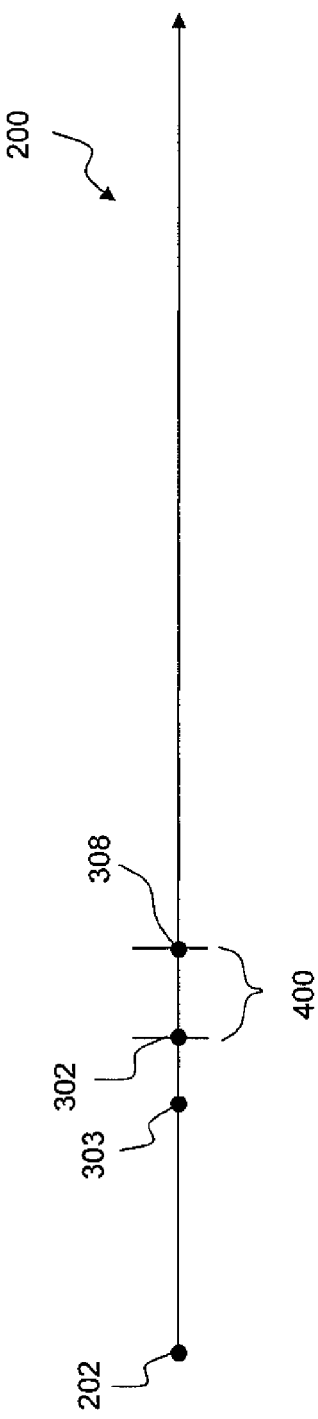

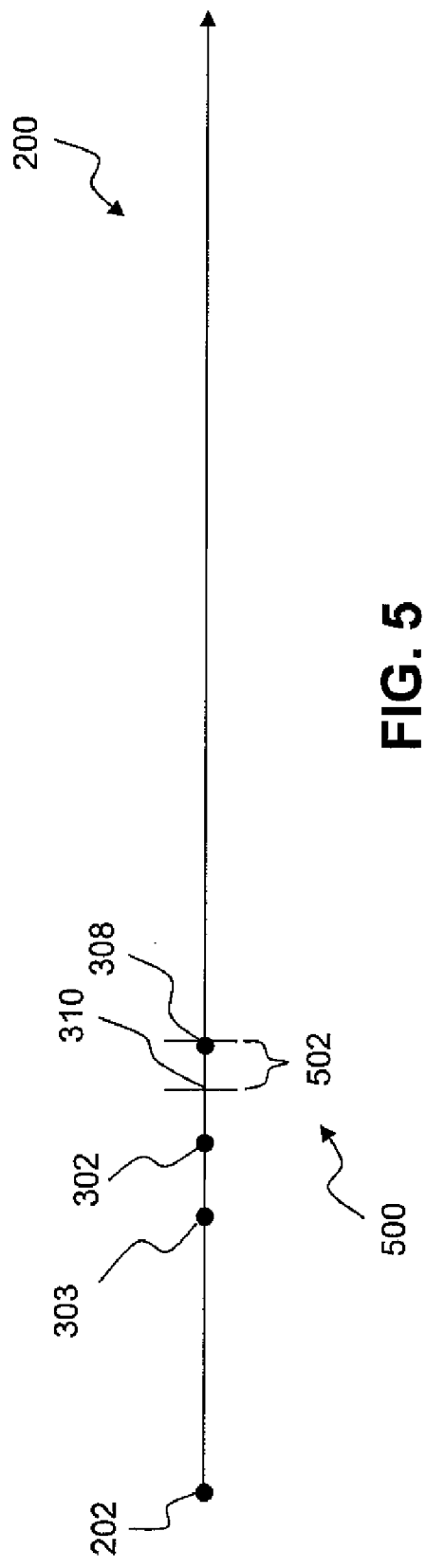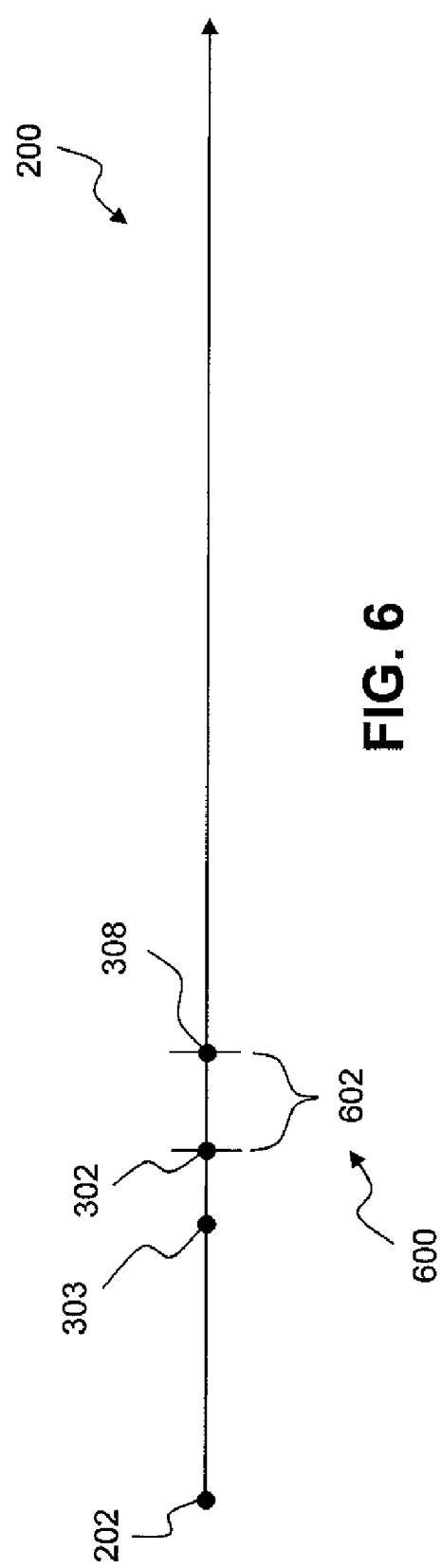

|  | Premeal | | | Postmeal | |
|---|---|---|---|---|---|
| Pair | Time | | BG | Time | | BG |
| 1 | 6/1/2006 | 6:51 AM | 103 | 6/1/2006 | 8:06 AM | 120 |
| 2 | 6/1/2006 | 11:30 AM | 110 | 6/1/2006 | 12:30 PM | 125 |
| 3 | 6/1/2006 | 6:30 PM | 97 | 6/1/2006 | 7:38 PM | 114 |
| 4 | 6/2/2006 | 6:55 AM | 101 | 6/2/2006 | 8:10 AM | 118 |
| 5 | 6/2/2006 | 11:36 AM | 107 | 6/2/2006 | 12:37 PM | 120 |
| 6 | 6/2/2006 | 6:44 PM | 100 | 6/2/2006 | 7:52 PM | 115 |
| * | * | | * | * | | * |
| * | * | | * | * | | * |
| * | * | | * | * | | * |
FIG. 7
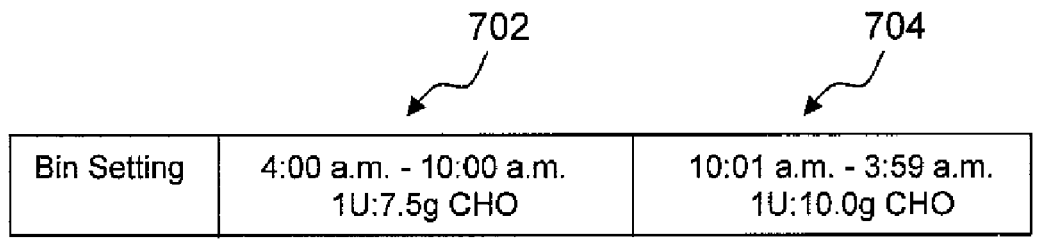
FIG. 8
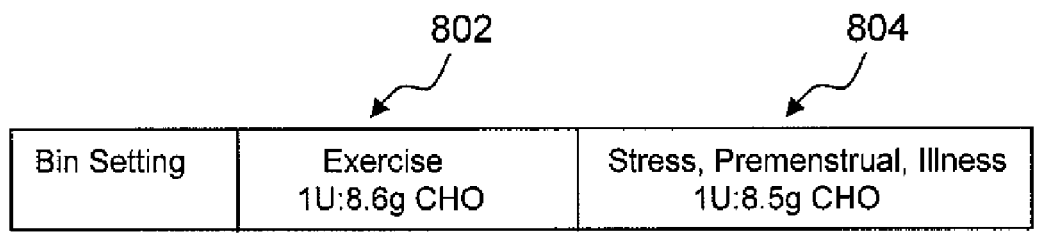
FIG. 9

MASK ALGORITHMS FOR HEALTH MANAGEMENT SYSTEMS

FIELD

The present disclosure relates generally to the administration of insulin in diabetics. More particularly, the present disclosure relates to a method for insulin dosage alterations for various conditions.

BACKGROUND AND SUMMARY

The art of self-care for a patient with Type-1 diabetes typically involves an assortment of professional Health Care counseling, hard-copy guide sheets provided by a Health Care Professional, self-care reading material and improvisation based on well established general principles of how the endocrine system operates.

Self-care devices such as those containing the Accu-chek® Advisor® Insulin Guidance Software allow a patient to enter data regarding their carbohydrate events, such as insulin doses and carbohydrate intakes, and blood glucose (BG) readings. The self-care device can then adjust recommended doses based upon the received data. The device adjusts the recommended doses based upon programming that is representative of a physician prescription. Accordingly, the healthcare provider is able to adjust the rules that dictate the dosing and dosing alterations as well as the doses themselves.

The healthcare provider can review the data from the self-care device either by local or remote reporting. The healthcare provider must be able to interpret the data in order to assess the performance of the current dosing regimen and to then make any necessary changes.

Accordingly, a method and process are provided that aid the healthcare provider in interpreting the health information.

According to one aspect of the present disclosure, a method of processing medical information is provided. The method includes the steps of receiving medical information relating to a dosing regimen; filtering the data using pre-determined parameters that are patient-input independent to provide a pair of pre-event and post-event data points; and displaying the pair of points.

According to another aspect of the present disclosure, a method of assessing efficacy of a regimen is provided. The method includes the steps of receiving medical information relating to an insulin dosing regimen; filtering the data using pre-determined parameters that are patient-input independent to provide qualified pairs of pre-carbohydrate ingestion and post-carbohydrate ingestion data points; and displaying the pairs of points.

According to another aspect of the present disclosure, a computer readable medium containing instructions that when executed by a computer performs steps to process medical information is provided. The steps comprising receiving medical information relating to a dosing regimen; filtering the data using pre-determined parameters that are patient-input independent to provide pairs of pre-event and post-event data points; and displaying the pairs of points.

Additional features of the present disclosure will become apparent to those skilled in the art upon consideration of the following detailed description of the presently perceived best mode of carrying out the disclosure.

BRIEF DESCRIPTION OF THE DRAWINGS

The detailed description of the drawings particularly refers to the accompanying figures in which;

FIG. 2 is an example timeline with data received from the PDA of FIG. 1;

FIG. 3 shows a first mask applied to the data timeline of FIG. 2;

FIG. 4 shows a second mask applied to the data timeline of FIG. 2;

FIG. 5 shows a third mask applied to the data timeline of FIG. 2;

FIG. 6 shows a fourth mask applied to the data timeline of FIG. 2;

FIG. 7 shows a first report able to be generated via the masking process depicted in FIGS. 3-6;

FIG. 8 shows a second report able to be generated via the masking process depicted in FIGS. 3-6;

FIG. 9 shows a third report able to be generated via the masking process depicted in FIGS. 3-6;

DETAILED DESCRIPTION OF THE DRAWINGS

Figure 1:
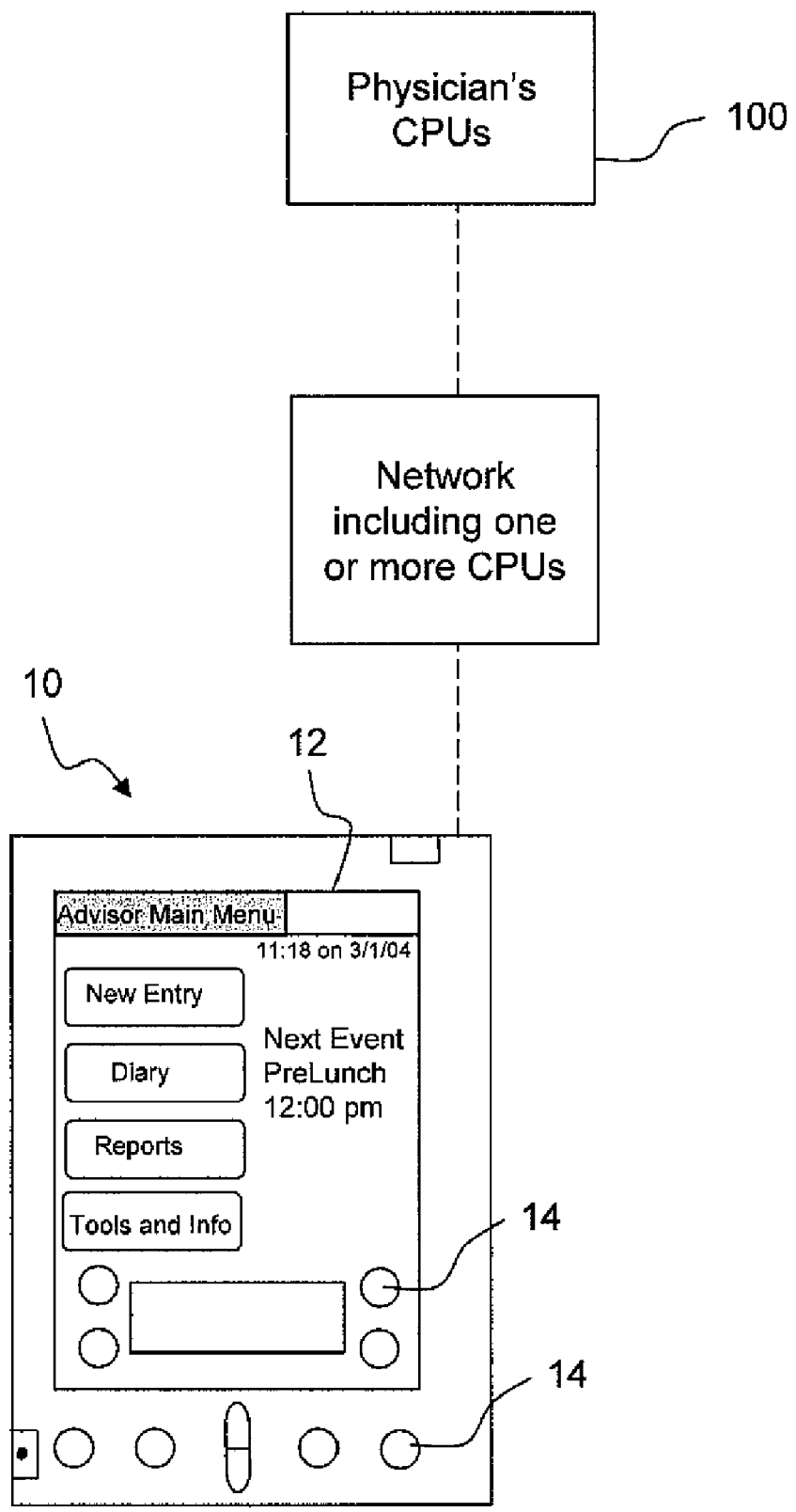
FIG. 1 is a personal digital assistant (PDA) capable of providing insulin dosing advice.

A PDA 10 is shown in FIG. 1 for providing insulin dosing advice to a user. PDA 10 includes a screen 12, a plurality of input devices 14 (which may include screen 12), a processor (not shown), and memory (not shown). Examples of PDA's are handheld computing devices made commercially available by Palm, Inc. and Handspring. While the methods and programs described herein may utilize data received from PDA 10, it should be appreciated that various devices or data collection devices and methods would also be acceptable alternatives to a PDA 10.

A patient enters data regarding carbohydrate events, such as meals, insulin administration, and blood glucose (BG) readings into PDA 10. PDA 10 is selectively connected to a desktop application such as a PC or a printer. PDA 10 downloads data to a web based server where the data can be reviewed by a health care professional via a remote computer 100. Alternatively, PDA 10 can be directly attached to remote computer 100. The connections may be wired or wireless. Alternatively, the healthcare professional can access the data directly on PDA 10. Both PDA 10 and computer 100 have software thereon to process data received from the patient. By reviewing the data, the healthcare provider can alter the insulin regimen of the patient.

A "regimen" consists of a battery of base doses, also referred to as usual doses. A regimen may be based on flexible or rigid timing for dosing. In the field of insulin dose therapy there are two kinds of alterations of these usual doses: adjustments and supplements. "Adjustments" are defined as persistent changes to usual doses, and supplements are defined as temporary changes to usual doses. The healthcare provider can specify alterations, supplements, as well as the conditions that cause such changes to be implemented.

To aid the healthcare professional in determining the dosing parameters, programs are provided that sift through the provided data to glean relevant data and present the relevant data in an easy to read format. Thus, the healthcare professional may quickly and easily be appraised of the most important factors for providing and altering a regimen.

Such programs are described herein as masks and are applied with reference to the exemplary data set of FIG. 2. The programs are described as masks in that they define a time period within which data is considered while ignoring data outside the time period. Accordingly, data outside the time period is "masked" off.

The data comes in the form of a data vector 200. Vector 200 starts at origin 202 and progresses in time showing the data points as they occur. Points on vector 200 may have labels placed upon the points by external sources, sources other than the mask algorithms discussed below. Vector 200 is analyzed to tag points of interest. Such tagging occurs independently of how any external source may have identified the points. One such point of interest is a meal or other carbohydrate intake event. Around a meal are other points of interest. Accordingly, vector 200 is analyzed to find suspected meal events. The program identifies the suspected meal events as a candidate and then attempts to identify pairs of premeal and postmeal candidate events. Each premeal candidate event has a corresponding postmeal candidate event.

A method of determining regimen efficacy is to analyze the BC levels one hour after a meal when rapid acting insulin boluses are being utilized. Using this method, the analysis begins at origin 202 of vector 200.

Four masks 300, 400, 500, 600 are successively applied to vector 200 to determine points of interest or "hits" that correspond to portions of vector 200 that fit conditions defined in at least one mask 300, 400, 500, 600. Masks 300, 400, 500, 600 filter the data points to find qualified points. In so doing, the patient is not asked or required to identify premeal or postmeal readings or to identify time periods in which such readings are believed to be located. Masks 300, 400, 500, 600 determine relevant points independently from user input, except for input of the data itself.

First mask 300 defines a two hour window within which the program attempts to identify a data point meeting defined conditions. Mask 300 progresses down vector 200 searching for events that match the defined rules. In other words, mask 300 starts at the two hour section immediately following origin 202. Once that time window is analyzed for meeting the criteria of mask 300, mask 300 progresses down vector 300 by one minute. It should be appreciated that while the present system is described as moving in one minute increments, other time increments may be used or analysis may skip from event entry point to event entry point. Once moved by the desired increment, the selected section of vector 200 is analyzed. This process is repeated in an iterative manner until all of vector 200 is analyzed. Hits are logged as mask 300 analyzes all of vector 200.

The defined conditions of first mask 300 include finding a carbohydrate intake that is at least two hours after any bolus application event. FIG. 3 shows how such a data point would be identified by first mask 300. Identified point 302 is located at the far right of the analyzed area of mask 300 in that mask 300 is two hours wide and also requires that no carbohydrate intake events be within the prior two hours. Hits gathered by mask 300 are candidates for showing a premeal event. Further analysis, discussed below, is applied to determine whether the gathered hits are truly of interest or need to be discarded.

The programming searches for a BG value taken at a time within a Premeal target range, illustratively shown as 30 minutes, of identified point 302. If the nearest BG value is outside the Premeal target range or missing altogether, point 302 is disqualified as being out of compliance with mask conditions and discarded. In such event, mask 300 shifts down vector 200 by the chosen increment and the identification process starts again. Alternatively, mask 300 may shift down by two hours from point 302 in that the presence of the carbohydrate event at 302 will prevent any other carbohydrate event within two hours thereof from satisfying the criteria of mask 300. To qualify as a Premeal BG value, the measurement must also indicate as satisfactory BG level (typically between 80-120 for Premeal BG).

If a BG value is found that was taken within the Premeal target range of the carbohydrate intake candidate, such as point 303, then the programming searches for a qualifying Postmeal BG value. In order to be a qualifying Postmeal BG value, the value must have been taken within a predefined time window. In the present example, mask 300 defines that a qualifying Postmeal BG value must have been taken within 50 to 80 minutes after candidate Premeal event 302. Accordingly, a thirty minute window 306 starting at 50 minutes after point 302 and ending 80 minutes after point 302 will be searched for a BG measurement and associated value. As shown in FIG. 3, such an inquiry would locate point 308.

Next, mask 400 is applied to data vector 200 as shown in FIG. 4. Mask 400 has a one hour, twenty minute window/ width. Mask 400 is applied to data vector 200 such that the previously identified candidate Premeal hit, point 302, is at the left-most edge of the window. If a BG value is detected in the last 30 minutes of mask 400, it is labeled as a candidate Postmeal BG value. In the provided example, mask 400 also locates point 308.

If more than one BG value is found in the windows, only the first instance is labeled as a candidate Postmeal BG value. Once found, the time interval between the candidate Premeal carbohydrate intake event, point 302, and the candidate Postmeal BG value, point 308, is determined. Accordingly, Interval t(PP)=t(candidate Postmeal)–t(candidate Premeal). If no candidate Postmeal BC value is identified, the candidate Premeal event is discarded and mask 300 is engaged to find another candidate Premeal event.

Mask 500 is then applied to vector 200 with respect to candidate Premeal event 302 as shown in FIG. 5. Mask 500 requires that no additional carbohydrate intake events exist between twenty minutes after the candidate Premeal event 302 and candidate Postmeal event 308. Thus, mask 500 defines window 502 that starts twenty minutes past point 302, labeled as 310, and extends to Postmeal candidate point 308. If a carbohydrate intake event is found within the window of mask 500, the Premeal and Postmeal candidates are discarded and mask 300 is moved along vector 200 in search of another Premeal candidate.

Assuming that the conditions of mask 500 are satisfied, mask 600 is then applied. Mask 600 disqualifies any candidates that have a BG correction (such as an injection of a rapid-acting bolus of insulin) between the candidate events 302, 308. Accordingly, as shown in FIG. 6, mask 600 is located such that the left-hand edge of window 602 is located at Premeal candidate 302. The right-hand edge of window 602 is located at Postmeal candidate 308. If a BG correction is found within window 602, candidate Premeal 302 and Postmeal 308 points are discarded and mask 300 is moved along vector 200 in search of another Premeal candidate.

Assuming the conditions of mask 600 are satisfied, candidate Premeal event point 302 and candidate Postmeal event point 308 are verified and are no longer referred to as "candidates." Rather, point 302 becomes Premeal event point 302 and point 308 becomes Postmeal event point 308. As previously noted, data points on vector 200 may have arrived with labels such as premeal BG level and postmeal BG level. As shown here, such external labels are not considered. Rather, the masks 300, 400, 500, 600 applies such labels itself after analyzing and qualifying the data.

Vector 200 is then analyzed to find any other carbohydrate intake values within twenty minutes after and including Premeal event point 302. This summation is generally referred to as carbohydrate intake compression in that many individual carbohydrate intake values are potentially compressed into a single summation value, the Premeal event value. The Premeal event value assumes the timestamp of Premeal event point 302. This Premeal event value and point 302 are paired with Postmeal value and event point 308 to result in an event pair of values and points. Upon achieving an event pair of values, the system moves mask 300 down vector 200 to find new candidate Premeal events. When mask 300 reaches the end of vector 200, the system proceeds to a data presentation phase.

Now that the data has been mined and properly qualified, the data can be presented to the healthcare professional in a number of ways. Five such ways are presented here as examples.

The first format, shown in FIG. 7, provides a single list of sequential pairs of Premeal and Postmeal BG values with timestamps. The second format, shown in FIG. 8, provides a number of insulin to carbohydrate ratios (ratio of insulin administered to carbohydrates ingested). A number of bins 702, 704 are determined in which to divide the data of the results vector, the values of which are shown in the first results format of FIG. 7. By example, the healthcare provider may wish to divide the data into two bins 702, 704. All data, both the Premeal and Postmeal data, having a Premeal timestamp between 4 a.m. and 10 a.m. are placed in first bin 702. The balance of the data is placed in second bin 704. Furthermore, the healthcare provider can choose a portion of the results vector on which to perform the sorting into bins 702, 704. For example, the healthcare provider may wish to only see the most recent week of data. Once the results vector is sorted into bins 702, 704, each bin 702, 704 can be processed. Within each bin, the Premeal values and Postmeal values are averaged, respectively, including the insulin administered and the carbohydrates consumed. Accordingly, each bin produces an insulin to carbohydrate ratio. Thus, the healthcare provider is able to view the general/average treatment and response for a given time of the day. The healthcare provider can adjust the number and parameters of the bins to get the desired targeting and specificity of the results.

Some data gathering devices, such as PDA 10, have the ability to record physiological conditions that effect their insulin requirements, such as exercise, stress, menstrual status, and whether or not the patient is experiencing illness. One such device is described in U.S. patent application Ser. No. 11/422,639, which is incorporated herein by reference. When such data is available, a third results format is provided, as shown in FIG. 9. The third results format allows further filtering of bins 700. The third format allows further sub-bins 802, 804 that show insulin to carbohydrate ratios for specific reported physiological conditions. Such ratios would assist the healthcare provider in altering settings in such a PDA 10 that has the ability to record and provide adjustments to a recommended dose for such physiological conditions.

Figure 10:
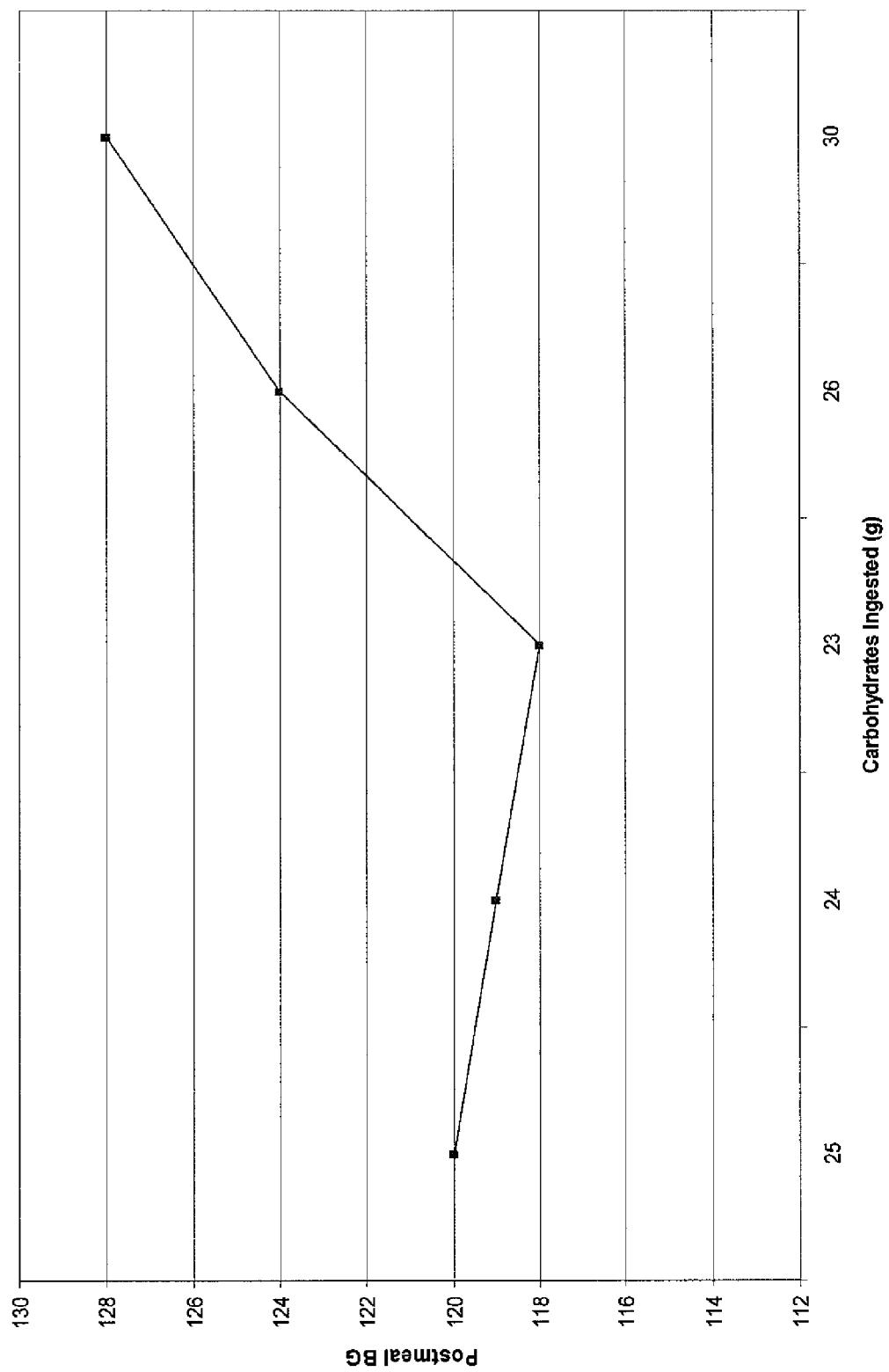
FIG. 10 shows a fourth report able to be generated via the masking process depicted in FIGS. 3-6.

A fourth results format is a graphical representation of the second results format. Whereas there are many ways to graphically express the results of the second format, FIG. 10 shows one example. FIG. 10 shows values sorted into bin 702 with their Premeal carbohydrate intakes plotted against Postmeal BG values. A variation of this format is also envisioned, but not shown, which involves the healthcare provider entering a preferred Postmeal BG upper threshold. All Postmeal BG values are reduced by the entered threshold. The adjusted Postmeal BG values are then plotted against the Premeal carbohydrate intakes.

Figure 11:
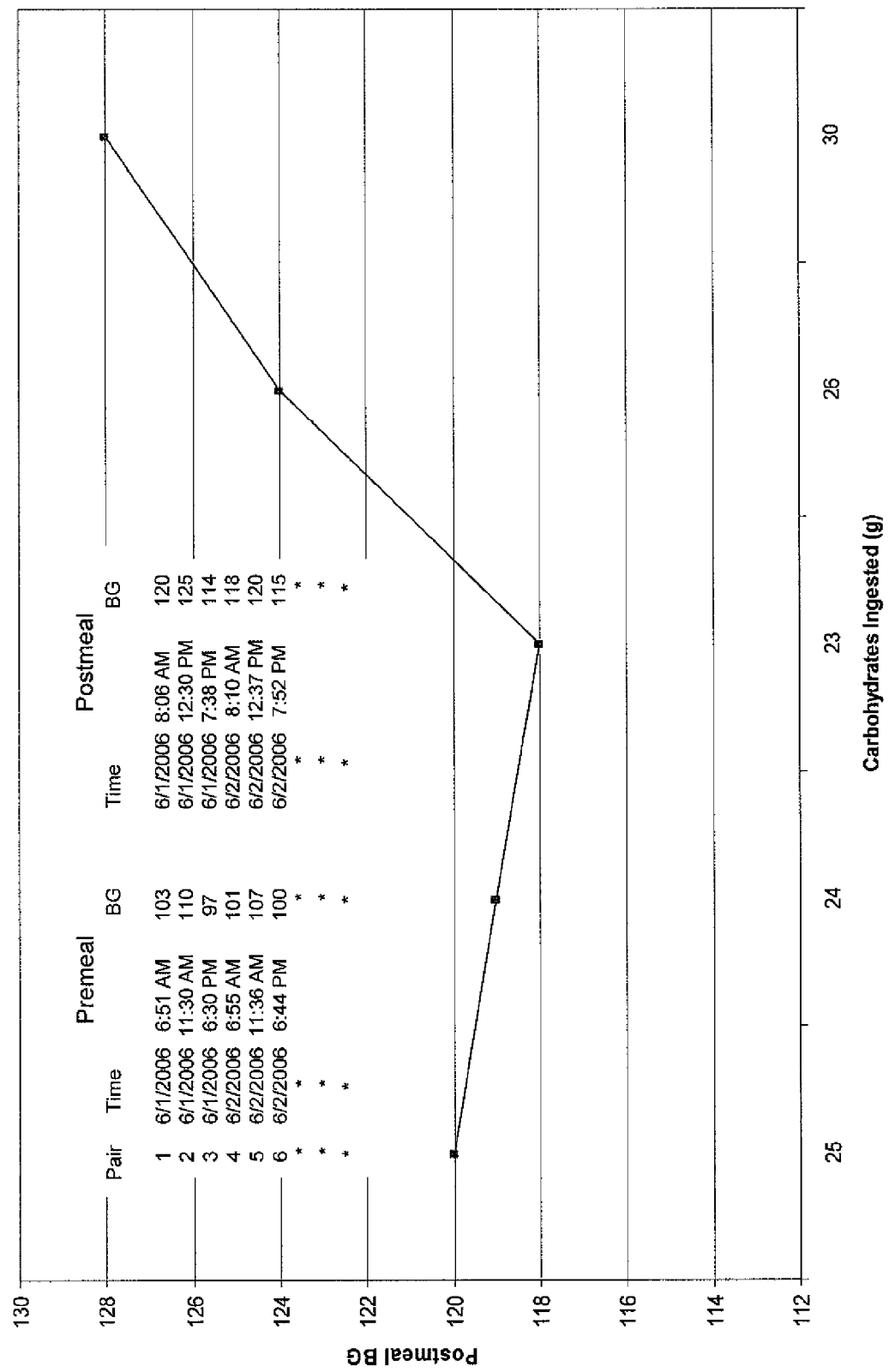
FIG. 11 shows a fifth report able to be generated via the masking process depicted in FIGS. 3-6.

A fifth results format is shown in FIG. 11. This format is simply a combination and simultaneous presentation of the first format of FIG. 7 and the fourth format of FIG. 10. The first through fourth results formats can be combined in other ways as desired by the healthcare provider.

If the above masking system fails to return any hits, the healthcare provider should know that there is a basal problem that must be corrected in advance of addressing any bolus problem.

As opposed to determining regimen efficacy by analyzing the BG levels one hour after a meal when rapid acting insulin boluses are being utilized, some healthcare providers believe that other measurement times are better suited for determining efficacy of a regimen. One such alternative teaches that recovery or near restoration of a BG level to a Premeal target-range high level (to within +/−20 mg/dl) is the proper goal at a 2-hour Postmeal location. Accordingly, the present disclosure anticipates alterations to masks 300, 400, 500, 600 to look for measurements responsive to this alternative method of determining efficacy.

Both the described and alternate methods of determining efficacy work equally well for regular insulin regimens, as opposed to the rapid-acting regimens described. Regular insulin has a 30-minute start of meal lag time as recommended by most manufacturers. When applying masks 300, 400, 500, 600 to regular insulin regimens, it should be appreciated that some windows may need to be extended in width by 30 minutes. Remote computer 100 has software that allows the healthcare provider to specify which efficacy measuring method he/she wishes to use and to specify whether the patient is on a rapid acting or a regular insulin regimen. Alternatively, the patient may enter the type of insulin used into PDA 10 such that the programming recognizes whether a rapid acting or regular insulin regimen is being utilized.

As described in previously referenced U.S. patent application Ser. No. 11/422,639, a patient may make alterations and supplements to the prescribed regimen. The above method allows data including such alterations and supplements to be filtered and scrubbed into a format that is easily viewed and understood by a healthcare provider. Thus, the decision making process of the healthcare provider is aided.

Although the disclosure has been described in detail with reference to certain preferred embodiments, variations and modifications exist within the spirit and scope of the disclosure as described and defined in the following claims.

The invention claimed is:

1. A method of processing medical information in a medical advising device including the steps of:
    receiving medical information relating to a dosing regimen by the medical advising device;
    filtering the data, in the medical advising device, using pre-determined parameters to provide a pair of pre-event and post-event data points, the filtering providing that the data points are identified independently of patient-input associated with the data points other than the numerical and unit value of the data points and independently of time of day associated with the data points; and
    displaying the pair of points by the medical advising device.

2. The method of claim 1, wherein the event is carbohydrate intake.

3. The method of claim 1, wherein the pre-event data point includes a timestamp.

4. The method of claim 1, wherein the pre-event data point includes a blood glucose reading associated therewith.

5. The method of claim 1, wherein the pair of points is determined independently of any external event label associated with either of the pair of points.

6. The method of claim 1, wherein one of the pre-determined parameters is that the pre-event data point is required to be within 30 minutes of a carbohydrate ingestion.

7. The method of claim 1, wherein one of the pre-determined parameters is that the post-event data point is required to be within an hour and twenty minutes of a carbohydrate ingestion.

8. The method of claim 1, wherein the dosing regimen is an insulin dosing regimen.

9. The method of claim 1, wherein each event is required to be associated with one and only one pre-event data point and one and only one post-event data point.

10. The method of claim 1, wherein the filtering step includes considering the relative timing of the data points.

11. The method of claim 1, wherein each of the pre-event and post-event data points are blood glucose values and the filtering provides that the data points are identified without considering any patient created association that links the data point with a particular carbohydrate event.

12. A method of assessing efficacy of a regimen in a medical advising device including the steps of:
receiving medical information relating to an insulin dosing regimen by the medical advising device;
filtering the data in the medical advising device using pre-determined parameters that consider the numerical and unit values of the data but are otherwise patient-input independent to provide qualified pairs of pre-carbohydrate ingestion and post-carbohydrate ingestion data points, the pairs of points being determined independently of any external event label associated with either of the pair of points; and
displaying the pairs of points by the medical advising device.

13. The method of claim 12, wherein each event is required to be associated with one and only one pre-event data point and one and only one post-event data point.

14. The method of claim 12, wherein the filtering step includes the step of identifying pre-event and post-event data points from a set of data points and the qualified pairs of data points are identified independently of patient-input that characterizes the input.

15. A non-transitory computer readable medium containing instructions that when executed by a computer performs steps to process medical information, the steps comprising:
receiving data including time-stamped blood glucose readings;
filtering the data using pre-determined parameters that are patient-input independent to provide pairs of pre-event and post-event blood-glucose data points, the pairs of blood glucose data points being determined independently of any patient generated event label associated with any data points within the medical information and independently of the time-of-day of the data points; and
displaying the pairs of points.

16. The non-transitory computer readable medium of claim 15, wherein each event is required to be associated with one and only one pre-event data point and one and only one post-event data point.

17. The non-transitory computer readable medium of claim 15, wherein the filtering step includes the step of identifying pre-event and post-event data points from a set of data points and the data points are identified independently of patient-input other than the values and units of the data points and independently of time of day associated with the data points.

18. A non-transitory computer readable medium containing instructions that when executed by a computer performs steps to process medical information, the steps comprising:
receiving medical information relating to a dosing regimen; filtering the medical information into pairs of pre-event and post-event data points, the filtering providing that the data points are identified independently of the time of day associated with the data points;
wherein the filtering utilizes pre-determined parameters that are patient-input independent other than the numerical and unit values of the data points; and
displaying the pairs of points.

19. The non-transitory computer readable medium of claim 18, wherein the filtering includes considering a time associated with the pre-event data point relative to a time associated with an event data point and considering a time associated with the post-event data point relative to the time associated with the event, such considerations being directed to the relative time between the data points and being independent of the time of day indicated by the data points.

* * * * *